United States Patent [19]

Gilman et al.

[11] 4,078,893
[45] Mar. 14, 1978

[54] CATALYST SYSTEM FOR THE DETECTION AND ELIMINATION OF HYDROGEN GAS

[75] Inventors: Sol Gilman, Rumson; Paul J. Bramhall, Tinton Falls, both of N.J.

[73] Assignee: The United States of America as represented by the Secretary of the Army, Washington, D.C.

[21] Appl. No.: 701,273

[22] Filed: Jun. 30, 1976

[51] Int. Cl.² .................. C01N 31/10; C01N 31/22; B01J 8/00; H01M 8/06
[52] U.S. Cl. ............................. 23/253 TP; 23/288 R; 23/288 K; 73/29; 252/430; 252/477 R; 423/219; 423/248; 423/580; 429/57
[58] Field of Search ............... 252/430, 447, 425.3, 252/477 R, 184, 181.6; 429/57, 42; 423/248, 219, 580; 23/253 TP, 288 K, 288 R; 73/29; 176/37, 16

[56] References Cited

U.S. PATENT DOCUMENTS

| | | | |
|---|---|---|---|
| 3,084,658 | 4/1963 | Schell | 23/253 TP |
| 3,085,424 | 4/1963 | Berg | 73/29 |
| 3,252,839 | 5/1966 | Langer et al. | 429/42 |
| 3,297,484 | 1/1967 | Niedrach | 429/42 |
| 3,388,004 | 6/1968 | Rosenblatt | 252/430 |
| 3,682,705 | 8/1972 | Petix | 429/42 |
| 3,849,539 | 11/1974 | Coleman | 423/219 |
| 3,930,890 | 1/1976 | Dietz | 252/477 R |
| 3,940,348 | 2/1976 | Lahme | 252/477 R |
| 3,969,481 | 7/1976 | Murray et al. | 423/219 |
| 3,976,510 | 8/1976 | Wihsel et al. | 429/57 |

*Primary Examiner*—Winston A. Douglas
*Assistant Examiner*—P. E. Konopka
*Attorney, Agent, or Firm*—Nathan Edelberg; Sheldon Kanars; Roy E. Gordon

[57] ABSTRACT

A catalyst system for the elimination of hydrogen gas which comprises a polytetrafluoroethylene-bonded catalyst layer of carbon mixed with platinum black, a porous polytetrafluoroethylene film on the side thereof which faces the gas flow, and a metal backplate, all integrally bonded together. The assembly is particularly useful for the elimination of hydrogen gas in sealed equipment housings, for example, those containing batteries. A similar system may also be used as a detector of hydrogen by utilizing a detector paper therewith which indicates the presence of water.

10 Claims, 4 Drawing Figures

CATALYST SYSTEM FOR THE DETECTION AND ELIMINATION OF HYDROGEN GAS

RIGHTS OF GOVERNMENT

The invention described herein may be manufactured and used by or for the Government for governmental purposes without the payment of any royalties thereon or therefor.

BACKGROUND OF THE INVENTION

This invention relates to a Teflon-bonded catalyst system for the detection and elimination of hydrogen gas in sealed equipment housings. In particular, it relates to a catalytic system for use with batteries.

There are many military and civilian applications in which a battery is incorporated into the hermetically or partially-sealed housing of electrical, electronic or mechanical equipment. Since most batteries produce some hydrogen gas while standing or during discharge or re-charge, an explosive hydrogen-air mixture can eventually result and be ignited by a spark or arc from the equipment in the housing. Examples thereof are magnesium or zinc primary cells used with radio sets and other communications equipment and rechargeable lead-acid, silver-zinc or nickel-cadmium cells used with communications equipment, sensor equipment, internal combustion motors or electrical relays.

For such applications, it is useful to have a non-detonating and reliable catalyst which will keep the concentration of hydrogen below the explosive limit (4.1%) of reaction with the oxygen in the air, and it is further advantageous to have a simple and non-detonating detector that will give warning of the presence of an unexpected large concentration of hydrogen. The detector may be used either by itself, to detect hydrogen without attempts at removal, or it may be used with a hydrogen-removal catalyst, to warn of the presence of hydrogen even though the catalyst itself will eventually eliminate the hazard.

The aforementioned "unexpected large concentration of hydrogen" could result from battery deterioration or failure of a structural member intended to impede the flow of hydrogen from the source to the electrical, electronic or mechanical equipment.

A specific problem solved by the present invention is the detection and removal of hydrogen from an Army AN/PRC-77 radio set. In this radio, very large volumes of $H_2$ are produced by the battery commonly used therewith. Most of this hydrogen escapes to the outer atmosphere through a vent in the battery box. However, some of the hydrogen can leak through the battery connector and find its way into the "sealed" electronics compartment. It appears that a leakage rate as high as 200 cc of $H_2$ per day is possible in this application if the connector is faulty. Even higher leakage rates will occur if the vent fails. With the 3400 cc. void volume of the electronics compartment, the entry of only 139 cc. of $H_2$ (a concentration of more than 4.1 volume percent $H_2$) could result in an explosive mixture. Hence, such leakage presents serious problems.

Accordingly, one of the objects of the present invention is to provide a system for the detection of hydrogen gas in sealed equipment housings.

Another object of the invention is to provide a catalyst system which eliminates hydrogen gas so as to prevent potential explosions.

BRIEF DESCRIPTION OF THE DRAWINGS

These and other objects and advantages of the invention will become apparent to those skilled in the art from a consideration of the following specification and claims, taken in conjunction with the accompanying drawings, wherein:

DETAILED DESCRIPTION OF THE INVENTION

In accordance with the invention, it has been found that a catalyst assembly comprising a Teflon (polytetrafluoroethylene) -bonded layer of carbon powder mixed with platinum black facing the gas phase with a metal backplate, for example, an aluminum backplate, integrally bonded together, meets the objectives outlined hereinabove. A porous Teflon sheet bonded to the catalyst layer, on the gas side moderates the reaction and waterproofs the catalyst so as to prevent "drowning" by product water. The aluminum backplate serves as a heat sink to prevent the catalyst from overheating and either destroying itself or triggering an explosion. This catalyst, when used with an adjacent drying agent (for example, silica gel, anhydrous calcium sulfate or the like) has been found to far exceed the requirements placed upon it for the AN/PRC-77 radio set. More particularly, for a 2 × 2 × 0.06 inch catalyst size (and until all atmospheric $O_2$ is finally exhausted), the catalyst will maintain the concentration of hydrogen well below 4.1 volume percent for flow rates of $H_2$ of 200 cc/day or, conversely, it will combine well over 200 cc per day of $H_2$ without allowing the $H_2$ concentration to rise above 4.1%. More quantitative definition of the catalyst reactivity for this and other applications will be discussed below.

The hydrogen removal catalyst of the invention has the following characteristics:

1. It has a very small volume to reactivity ratio.
2. It is capable of dealing with high inflow rates of hydrogen.
3. It will not trigger an explosion even under the most rigorous conditions, including a sudden exposure to a 30% $H_2$-air mixture.
4. It functions well over the temperature range of −40° to 80° C.

Figure 1:
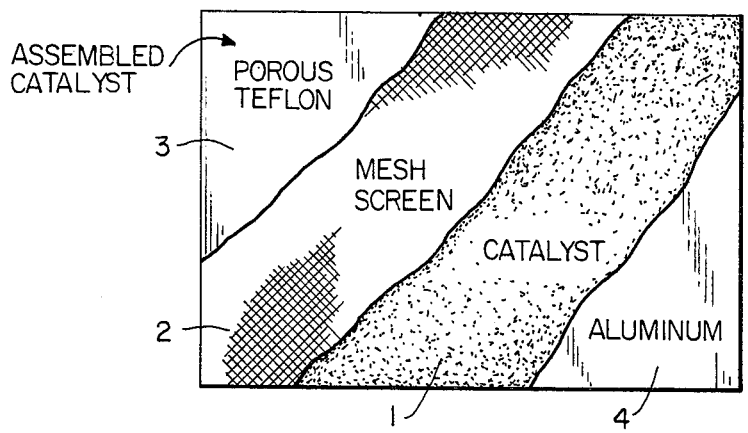
FIG. 1 is a schematic representation of the Teflon-bonded catalyst of the invention.

FIG. 1 illustrates a suitable Teflon-bonded catalyst made in accordance with this invention. A polytetrafluoroethylene (DuPont trade name, "Teflon")-bonded layer of a carbon black-Pt black mixture (5.2% Pt) 1 is bonded to a screen 2 (for example, a nickel screen), and a porous polytetrafluoroethylene sheet 3 is then bonded to the gas side thereof. The lower side of this assembly is cemented to a sheet of aluminum 4. The carbon serves as a diluent, heat sink and gas diffusion barrier for the active Pt particles. The metal sheet of aluminum acts as an additional heat sink and the porous Teflon acts as an additional gas diffusion barrier. Pt black, by itself, would ignite H$_2$-air mixtures, but has a lesser tendency to do so than Pd black. Without the heat sink and porous Teflon barrier, the structure would tend to overheat and self-destruct.

A catalyst structure as outlined above, having the dimensions of 2 × 2 × 0.06 inch, a volume of 0.24 cubic inches and a Pt loading of 1 mg/cm$^2$, exceeds the reactivity requirements for the AN/PRC-77 radio set discussed above and leaves ample room for incorporation of a large quantity of drying agent for removal of product water.

Figure 2:
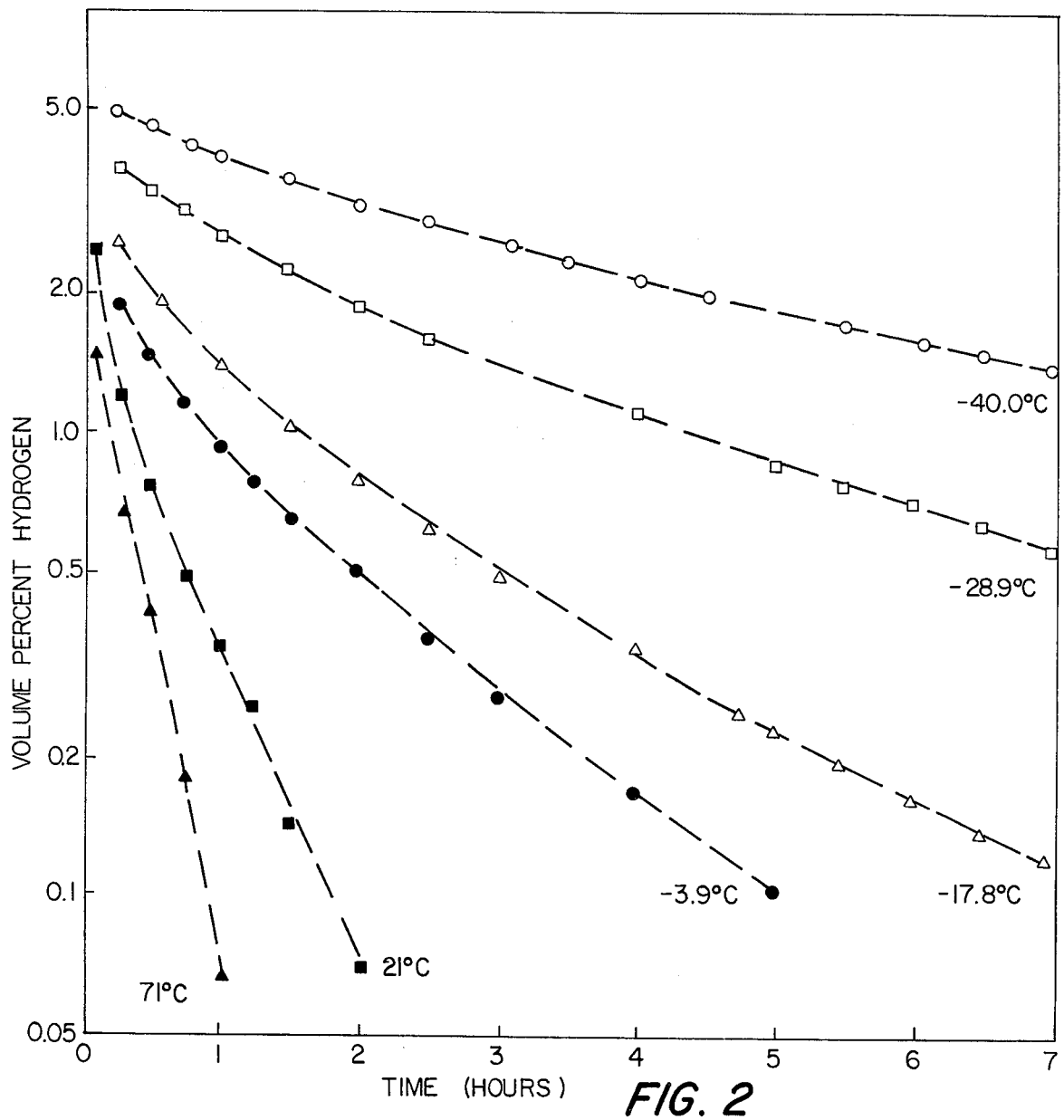
FIG. 2 is a graph showing the variation of hydrogen concentration (after initial introduction of 300 cc of pure $H_2$) in the electronics compartment of an AN/PRC-77 radio set equipped with a Teflon-bonded catalyst made according to the description hereinbelow.

The reactivity of the catalyst can be defined in terms of an "apparent specific rate," $k_t$, which can be determined from the time response of hydrogen concentration after introduction of a hydrogen aliquot (i.e., from plots such as those of FIG. 2). After the first few hours, the plots are approximately linear, suggesting the following relationship:

$$\frac{-d\ln p}{dt} = k_t p \quad (1)$$

where $p$ is any measure of partial pressure or concentration of hydrogen, including volume percent, $t$ is the time (in hours) and $k_t$ (hours$^{-1}$) is the slope of the linear portion of the plot for any temperature, $t$. The slope, $k_t$, is an "apparent specific rate" for the particular size of the catalyst and for the 3400 cc reaction volume of the present AN/PRC-77 application. From equation (1), the following relationship can be derived:

$$-\frac{dp}{dt} = k_t p \quad (2)$$

Although $k_t$ was obtained from experiments in which the entire quantity (300 cc) of H$_2$ was introduced at the beginning of the run, that "apparent specific rate" may be used to calculate the response of the system to flow conditions or to calculate the value of $k_t$ required to prevent the concentration of H$_2$ from rising above a maximum value in the face of a specified rate of inflow of H$_2$. For example, the AN/PRC-77 radio mentioned above required that the catalyst eliminate at least 200 cc of H$_2$ per day while not allowing the concentration of H$_2$ to rise above 4.1%. A 200 cc per day inflow of H$_2$ into a reaction volume of 3400 cc and subsequent reaction with O$_2$ is equivalent to $-dp/dt=0.25$ volume percent per hour. Setting p at 4.1%, it can be determined from equation (2) that $k_t$ must have the value 0.06 hour$^{-1}$. From FIG. 3 it can be seen that $k_t$ always exceeds 0.06 hour$^{-1}$. As a second example of the application of equation (2), the concentration of H$_2$ likely to result can be calculated, at 20° C., for an inflow of 200 cc/day of H$_2$ into the AN/PRC-77 radio set using the catalyst of the invention. From FIG. 3, $k_t$ at 20° C. has the value 1.3 hour$^{-1}$. for $dp/dt=0.25$ volume percent per hour, equation (2) predicts that $p$ will eventually have the value 0.19 volume percent H$_2$ which is well below our minimum requirement that $p$ be below 4.1 volume percent. A third example of the application of equation (2) is in the calculation of the maximum inflow rate of H$_2$ which can be tolerated at 20° C. without allowing the concentration of H$_2$ to rise above 4.1 volume percent. Substituting $p=4.1\%$ and $k_t=1.3$ hour$^{-1}$ in equation (2), the value of 5.33 percent per hour for $dp/dt$ is obtained. This is equivalent to a H$_2$ inflow rate of 4,349 cc/day which is much greater than the 200 cc per day maximum inflow anticipated for the AN/PRC-77 requirement.

It must be noted that calculations based on equation (2) are for a "quasi-steady-state" condition which can exist for as long as the concentration of oxygen in the enclosed space remains higher than the hydrogen concentration. However, once the O$_2$ concentration level drops below 4.4%, the mixture is no longer combustible and therefore the decline in H$_2$ oxidation rate becomes unimportant from a practical point of view.

Figure 3:
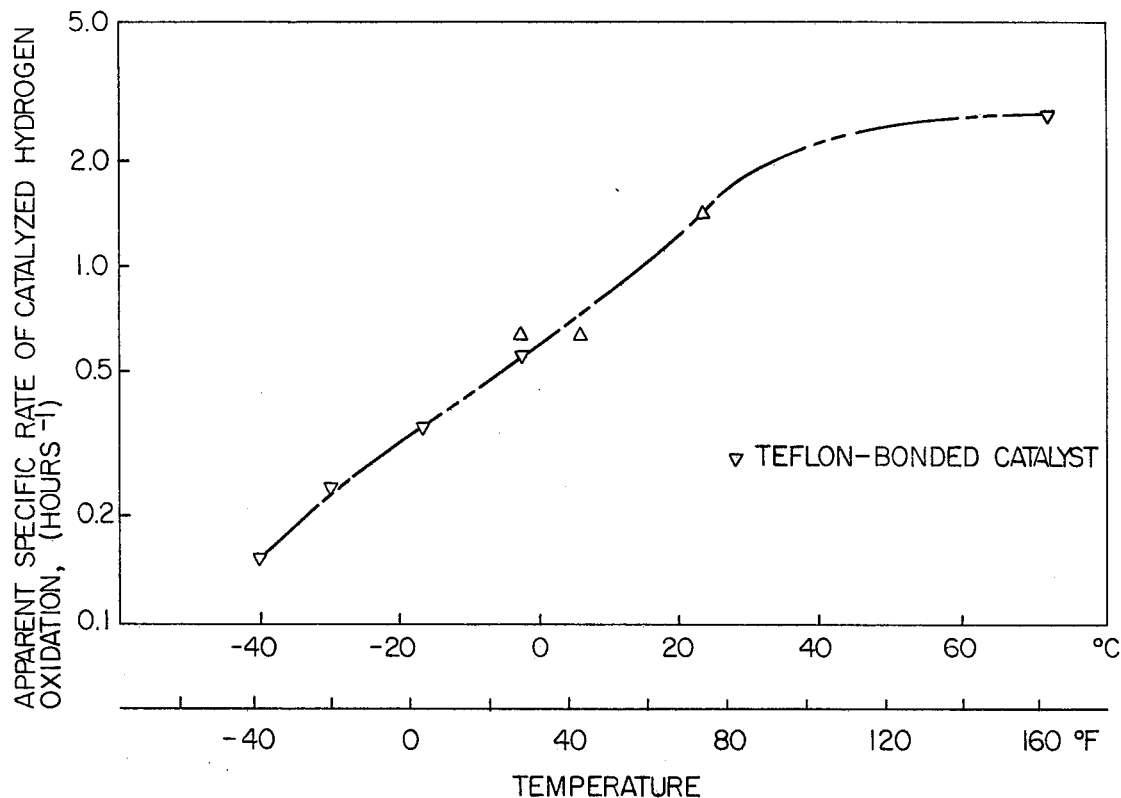
FIG. 3, derived from the data of FIG. 2, is a graph showing the "apparent specific hydrogen oxidation rate" of the Teflon-bonded catalyst in the electronics compartment of an AN/PRC-77 radio set.

The values of $k_t$ given in FIG. 3 hold for the specific size of catalyst described herein (2 × 2 inches) and for a 3400 cc gas volume. For any other condition, a new value of "apparent specific rate" may be calculated using equation (4):

$$k_t' = k_t \cdot \frac{S}{4} \cdot \frac{3400}{V} \quad (4)$$

where $k_t'$ is the new "apparent specific rate" for the system, S is the size (in square inches) of the new catalyst and V is the void volume (in cubic centimeters) of the new container.

A comparison of reactivity was made between the catalyst of the present invention and the catalyst pellets described in lines 19-44, col. 8 of U.S. Pat. No. 3,630,778. At $-5°$ C. eight pellets as described in said patent were required to achieve the minimal requirement of $k_t=0.06$ hour$^{-1}$ in the AN/PRC-77 radio set. The eight pellets had a total volume of 0.38 cubic inches. Under the same conditions, according to FIG. 3, the catalyst of this invention, with dimensions of 2 × 2 × 0.06 inch has a $k_t$ value of 0.5 hour$^{-1}$. To make a comparison of catalyst volumes between our catalyst and the catalyst of the aforementioned U.S. Pat. No. 3,630,778, we set $k_t'$ of equation (4) to 0.06 hour$^{-1}$ and derived a value of S of 0.48 square inches for the required product of catalyst length by width. For a catalyst thickness of 0.06 inch, the required volume of catalyst would be 0.03 cubic inches or approximately one-thirteenth the volume of the required catalyst pellets of said patent. The minimization of catalyst volume as achieved in the present invention is an important factor and represents a beneficial characteristic of the invention.

The major problem in designing a suitable catalyst system for hydrogen removal is to obtain the highest possible rate of heterogeneous oxidation without introducing any significant likelihood of triggering the corresponding homogeneous chain reaction (detonation). If conditions were restricted to a gradual flow of hydrogen into air, the most active catalyst would likely not cause a detonation since it would not allow the concentration of H$_2$ in the vicinity thereof to build up to an explosive level. The situation with electronic and electrical equipment is, however, complicated by the necessity for periodically opening the electronics compartment to the air for servicing. This raises the possibility of rapidly mixing external air with an otherwise non-inflammable mixture of H$_2$ and N$_2$ (O$_2$ being exhausted by catalytic action) in the presence of an over-active catalyst. On that basis, it is prudent to consider a catalyst as being acceptable only if (1) it will not cause ignition of H$_2$-air mixtures under extreme conditions and (2) it will not suffer damage to itself from over-heating under extreme conditions. Accordingly, several catalysts were subjected to observation under two different test conditions:

1. Air leak (20 seconds) into pure $H_2$ at 0.3 atmosphere initial pressure to total final pressure of 1 atmosphere and $H_2$ concentration of 30%.
2. Instantaneous release of the catalyst into a premixed 30% $H_2$-air mixture at 1 atmosphere total pressure.

The results of these tests are summarized in Table 1.

The experiments with pure Pd black and Pt black were performed for comparison with catalysts having a practical configuration, and were the only materials which triggered explosions. In common with the catalyst of U.S. Pat. No. 3,630,778 the catalyst of this invention was found to be both safe and stable. In addition, the heat sink which serves as an integral part of the catalyst of this invention was found to be vital to its stability, for otherwise the catalyst "shrivels and delaminates" when exposed to extreme conditions, as shown in Table 1.

OBSERVATIONS OF DELETERIOUS EFFECTS FOR CATALYSTS EXPOSED TO EXTREME CONDITIONS

| Test Condition: Catalyst | OBSERVATIONS Surge of Air Into Pure Hydrogen | Instantaneous Exposure to 30% $H_2$-Air Mixture |
|---|---|---|
| Pure Pd Black* | Glows | Explodes |
| Pure Pt Black* | Glows | Explodes |
| Inner Pellet (U.S. Pat. 3,630,778) | No problem | No problem |
| Catalyst of the invention without the aluminum heat sink | Shrivels and Delaminates | Shrivels and Delaminates |
| Catalyst of the Invention | No problem | No problem |

*Milligram samples smeared on Teflon tape.

Figure 4:
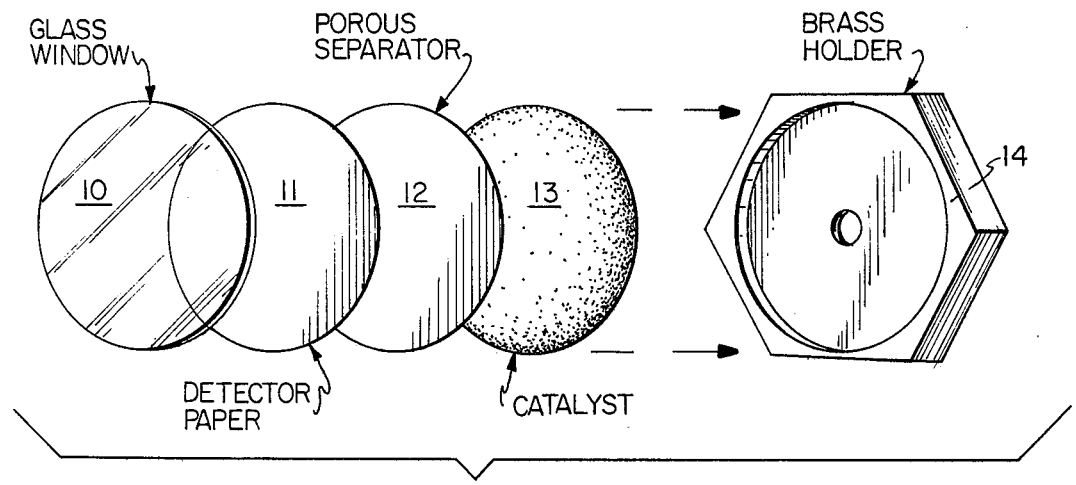
FIG. 4 is a schematic representation of a hydrogen detector utilizing the catalytic layer of the Teflon-bonded catalyst of the invention.

A simple hydrogen detector may be constructed utilizing the flat Teflon-bonded catalyst described herein. FIG. 4 illustrates the embodiment of the invention in this regard. The catalyst sensor consists of the Teflon-bonded catalyst 13 of the invention, less the metal support/heat sink. One side of the catalyst layer is covered with a porous Teflon film (being on the underside of the catalyst layer and not shown in FIG. 4), this side communicating with the gas flow by means of a small hole in the brass holder 14, holder 14 itself being threaded to fit into the electronics compartment of the particular equipment in which the detector is installed. The other side of the catalyst contacts a thin porous separator or spacer 12, such as a porous Teflon sheet, and a piece of detector paper 11 saturated with $CoCl_2$, the latter exhibiting a blue coloration in dry air and a pink coloration when moistened by catalytically-produced water. The color is viewed through the glass window 10 of the holder.

If no internal catalyst is used, the sensor will turn and remain pink after it produces enough water to moisten the paper. If an internal catalyst and an effective drying agent are used, the internal humidity of the electrical equipment will not rise sufficiently high to directly moisten the sensitive paper. Unreacted hydrogen gas can, however, seep in and cause a color change. Since the diffusivity of water vapor is only 38% that of hydrogen gas, the pink coloration will lag while the product water slowly evaporates and diffuses back out into the dry hydrogen-free (because of the internal catalyst) environment of the equipment. When the drying agent is depleted due to long or heavy use, the sensitive paper will again turn pink. Hence, in the presence of an internal catalyst, it is possible to sense the introduction of $H_2$ (blue to pink), the effectiveness of the catalyst in reducing the internal $H_2$ concentration (pink to blue) and the exhaustion of the drying agent (blue to pink). Without an internal catalyst, the detector of FIG. 4 shows a color indication, for example, within five hours after injecting enough hydrogen to produce a 1% $H_2$-air mixture in the electronics compartment of an AN/PRC-77 radio set. With a 2 × 2 inches Teflon-bonded internal catalyst and the injection of 300 cc. of $H_2$ (initial concentration of 8.11%), the indicator began to turn pink within two hours, remained pink for at least five more hours and turned blue within the next day or so as the water in the detector was drawn out into the interior of the then hydrogen-free and low humidity electronics compartment. The various color reaction times can, of course, be adjusted to different desired sensitivities by varying, for instance the diameter of the hole leading to the detector, the size of the detector and the thickness and porosity of the indicator paper.

The following Example is given merely as illustrative of the present invention and is not to be considered as limiting.

EXAMPLE

A cylindrical vessel was employed for the catalyst evaluation in order to provide a small, unbaffled gas space. The vessel had a volume of 960 cc.. It was designed to accomplish gas-tight closure by means of an O-ring kept under light pressure by a spring and wing-nut arrangement holding the lid in place. Since the tests were conducted at close to atmospheric pressure, the closure mechanism provided for pressure release in case of hydrogen explosion. A rubber septum permitted introduction of hydrogen aliquots and removal of gas samples by a syringe. A solenoid placed in the exhaust line permitted remote and rapid introduction or removal of air or mixtures of gas as required. A window in the cover made it possible to view the catalyst during a test. Remote viewing was accomplished by means of a mirror.

A Teflon-bonded catalyst was prepared comprising a carbon powder-platinum black-polytetrafluoroethylene mixture supported on a nickel screen. A porous polytetrafluoroethylene membrane was bonded to the side of the catalyst facing the reacting gas to serve as a gas diffusion barrier. A 2 × 2 inches square of 0.040 inch thick aluminum was bonded to the reverse side of the catalyst layer to act as a heat sink.

This assembly was obtained by pressing a 2 × 2 × 0.012 inch nickel screen into a 2½ × 2½ inches square of Zitex Teflon TFE No. HV100 membrane (0.004 inch thick) using a pressure of 30,000 psi. A mixture of 0.0258 g. of Pt black (Englehard Co.), 0.38 g. of Shawinigan carbon black and a Teflon emulsion containing 0.1 g. of Teflon TFE was blended with 10 cc. of water and the mixture applied to the nickel screen by means of a spatula. The assembly was pressed at 12,000 psi, air-dried and then vacuum-dried at 115° C.. The assembly was then trimmed to 2 × 2 inches and cemented with the Zitex membrane up, to the aluminum square using G.E. silicone rubber on the outer edge of the catalyst-membrane assembly.

A measurement of hydrogen oxidation rates was conducted starting with 8.1 volume percent hydrogen-air mixtures. For this test, the catalyst was placed in the chamber with some drying agent, and the chamber was sealed. An 85 cc. volume of air was withdrawn by a syringe and replaced with an 85 cc. volume of hydrogen. The concentration of hydrogen was then monitored by periodically withdrawing 0.5 cc. of gas an analyzing with a gas chromatograph. The results obtained show a roughly linear relationship over a wide temperature range when the logarithm of the hydrogen concentration is plotted against the reaction time.

Thus, it is clear that the catalyst of the invention is useful and reliable in rapidly oxidizing hydrogen to water so as to maintain the concentration of hydrogen within acceptable limits, thereby preventing potential explosions. As outlined above, the catalyst of the invention may also be modified to provide a detector structure to be employed either by itself to detect hydrogen or together with said hydrogen-removal catalyst. The catalyst functions efficiently over a wide range of temperature and therefore meets a long-felt need in the art.

Although the catalyst system of the invention has been described with certain specific materials for the purpose of clarity, it is to be understood that various modifications can be made therein. For example, the carbon powder may comprise either a graphitic powder or an amorphous powder, such as carbon black, or combinations thereof. Moreover, other high surface area powders capable of catalyzing hydrogen oxidation besides Pt black can be employed, such as Pd black, Rh black, Ir black or Ni powder. The binder for the catalyst layer as well as the porous film separators utilized in the catalyst system are hydrophobic and may comprise other fluorocarbon polymers such as fluorinated ethylene-propylene polymers, in addition to the polytetrafluoroethylene exemplified above.

The invention being thus described, it will be obvious that the same may be varied in many ways. Such variations are not to be regarded as a departure from the spirit and scope of the invention, and all such modifications are intended to be included within the scope of the following claims.

We claim:

1. A catalyst system for the detection and elimination of hydrogen gas in the presence of oxygen which comprises a catalyst layer of carbon powder mixed with a high surface area powder capable of catalyzing hydrogen oxidation in a fluorocarbon polymer binder, wherein said high surface area powder is selected from the group consisting of platinum black, palladium black, rhodium black, iridium black, and nickel powder, a first porous hydrophobic polymer film disposed on one side of said catalyst layer, a second thin spacer film disposed on the other side of said catalyst layer, and a detector paper which detects the presence of water, said detector paper being in contact with said spacer film.

2. A catalyst system according to claim 1, wherein said porous hydrophobic polymer film is a fluorocarbon polymer.

3. A catalyst system according to claim 1, wherein said spacer film is a fluorocarbon polymer.

4. A catalyst system for the detection and elimination of hydrogen gas in the presence of oxygen which comprises a polytetrafluoroethylene-bonded catalyst layer of carbon powder mixed with platinum black, a first porous polytetrafluoroethylene film disposed on one side of said catalyst layer, a second thin spacer film disposed on the other side of said catalyst layer, and a detector paper which detects the presence of water, said detector paper being in contact with said spacer film.

5. A catalyst system according to claim 4, wherein said detector paper is saturated with $CoCl_2$.

6. A catalyst system according to claim 4, which is disposed in a metal holder having a viewing window for said detector paper.

7. A catalyst system according to claim 4, wherein said thin spacer film is polytetrafluoroethylene.

8. A catalyst system according to claim 4, wherein said catalyst layer comprises a carbon powder-platinum black-polytetrafluoroethylene mixture supported on a metal screen.

9. A catalyst system according to claim 8, wherein said carbon powder is carbon black.

10. A catalyst system according to claim 8, wherein said metal screen is a nickel screen.

* * * * *